US008709050B2

(12) United States Patent
Shluzas

(10) Patent No.: US 8,709,050 B2
(45) Date of Patent: *Apr. 29, 2014

(54) METHODS FOR CONNECTING A LONGITUDINAL MEMBER TO A BONE PORTION

(75) Inventor: Alan E. Shluzas, Redwood City, CA (US)

(73) Assignee: Zimmer Spine, Inc., Minneapolis, MN (US)

( * ) Notice: Subject to any disclaimer, the term of this patent is extended or adjusted under 35 U.S.C. 154(b) by 268 days.

This patent is subject to a terminal disclaimer.

(21) Appl. No.: 13/013,257

(22) Filed: Jan. 25, 2011

(65) Prior Publication Data

US 2011/0118793 A1    May 19, 2011

Related U.S. Application Data

(63) Continuation of application No. 11/415,676, filed on May 2, 2006, now Pat. No. 7,879,075, which is a continuation of application No. 10/075,668, filed on Feb. 13, 2002, now Pat. No. 7,066,937.

(51) Int. Cl.
*A61B 17/70* (2006.01)

(52) U.S. Cl.
USPC .......................................................... 606/270

(58) Field of Classification Search
USPC .................... 606/246, 264–275, 278, 279
See application file for complete search history.

(56) References Cited

U.S. PATENT DOCUMENTS

| 5,005,562 A | 4/1991 | Cotrel |
| 5,135,489 A | 8/1992 | Jepson et al. |
| 5,207,678 A | 5/1993 | Harms |
| 5,443,467 A | 8/1995 | Biedermann et al. |
| 5,466,237 A | 11/1995 | Byrd et al. |
| 5,474,555 A | 12/1995 | Puno et al. |

(Continued)

FOREIGN PATENT DOCUMENTS

WO    03068083 A1    8/2003

OTHER PUBLICATIONS

DePuySpine, "Speed Security and Simplicity in Harmony, Expedium Spine System," 6 pages, Aug. 2004.

*Primary Examiner* — Anu Ramana
(74) *Attorney, Agent, or Firm* — Seager, Tufte & Wickhem, LLC

(57) ABSTRACT

An apparatus (10) includes a fastener (16) engageable with a bone portion to connect a longitudinal member (12) to the bone portion. A housing (40) has a first passage (42) configured to receive the longitudinal member (12) and a second passage (44) extending transverse to the first passage. The fastener (16) extends through an opening (50) in the housing (40) into the second passage (44). A longitudinal axis (18) of the fastener (16) is positionable in any one of a plurality of angular positions relative to a longitudinal axis (46) of the second passage (44). A spacer (60) received in the second passage (44) of the housing (40) is engageable with the fastener (16) and the longitudinal member (12). A member (70) applies a force to prevent relative movement between the fastener (16) and the housing (40) and permit manual movement of the fastener (16) relative to the housing (40) against the force when the longitudinal member (12) is disengaged from the spacer (60). A clamping mechanism (90) clamps the longitudinal member (12), the spacer (60), and the housing (40) to the fastener (16) to prevent movement of the fastener relative to the housing.

16 Claims, 3 Drawing Sheets

(56) References Cited

U.S. PATENT DOCUMENTS

| | | |
|---|---|---|
| 5,476,464 A | 12/1995 | Metz-Stavenhagen |
| 5,613,968 A | 3/1997 | Lin |
| 5,639,074 A | 6/1997 | Greenhill |
| 5,669,911 A | 9/1997 | Errico et al. |
| 5,672,176 A | 9/1997 | Biedermann |
| 5,690,630 A | 11/1997 | Errico et al. |
| 5,733,285 A | 3/1998 | Errico et al. |
| 5,797,911 A | 8/1998 | Sherman |
| 5,817,094 A | 10/1998 | Errico et al. |
| 5,876,402 A | 3/1999 | Errico et al. |
| 5,879,350 A | 3/1999 | Sherman |
| 5,885,286 A | 3/1999 | Sherman et al. |
| 6,010,503 A | 1/2000 | Richelsoph et al. |
| 6,022,350 A | 2/2000 | Ganem |
| 6,063,090 A | 5/2000 | Schlapfer |
| 6,074,391 A | 6/2000 | Metz-Stavenhagen |
| 6,077,262 A | 6/2000 | Schlapfer et al. |
| 6,090,110 A | 7/2000 | Metz-Stavenhagen |
| 6,090,111 A | 7/2000 | Nichols |
| 6,113,601 A | 9/2000 | Tatar |
| 6,139,550 A | 10/2000 | Michelson |
| 6,238,396 B1 | 5/2001 | Lombardo |
| 6,248,105 B1 * | 6/2001 | Schlapfer et al. ............ 606/266 |
| 6,261,287 B1 | 7/2001 | Metz-Stavenhagen |
| 6,280,442 B1 | 8/2001 | Barker et al. |
| 6,287,311 B1 | 9/2001 | Sherman |
| 6,296,642 B1 | 10/2001 | Morrison et al. |
| 6,302,888 B1 | 10/2001 | Mellinger et al. |
| 6,375,657 B1 | 4/2002 | Doubler et al. |
| 6,402,752 B2 | 6/2002 | Schaffler-Wachter |
| 6,440,137 B1 | 8/2002 | Horvath et al. |
| 6,454,768 B1 | 9/2002 | Jackson |
| 6,471,705 B1 | 10/2002 | Biedermann |
| 6,485,491 B1 | 11/2002 | Farris et al. |
| 6,488,681 B2 | 12/2002 | Martin et al. |
| 6,511,099 B2 | 1/2003 | Bartholoma et al. |
| 6,530,929 B1 | 3/2003 | Justis et al. |
| 6,537,276 B2 | 3/2003 | Metz-Stavenhagen |
| 6,540,748 B2 | 4/2003 | Lombardo |
| 6,547,725 B1 | 4/2003 | Paolitto et al. |
| 6,551,323 B2 | 4/2003 | Doubler et al. |
| 6,565,565 B1 | 5/2003 | Yuan et al. |
| 6,565,567 B1 | 5/2003 | Haider |
| 6,585,740 B2 | 7/2003 | Schlapfer |
| 6,726,687 B2 | 4/2004 | Jackson |
| 6,755,829 B1 | 6/2004 | Bono et al. |
| 6,835,196 B2 | 12/2004 | Biedermann et al. |
| 6,837,889 B2 | 1/2005 | Shluzas |
| 6,869,433 B2 | 3/2005 | Glascott |
| 7,018,378 B2 | 3/2006 | Biedermann et al. |
| 7,066,937 B2 | 6/2006 | Shluzas |
| 7,144,396 B2 | 12/2006 | Shluzas |
| 7,604,656 B2 | 10/2009 | Shluzas |
| 2001/0001119 A1 | 5/2001 | Lombardo |
| 2002/0091386 A1 | 7/2002 | Martin et al. |
| 2002/0138076 A1 | 9/2002 | Biedermann et al. |
| 2003/0004512 A1 | 1/2003 | Farris et al. |
| 2004/0153068 A1 | 8/2004 | Janowski et al. |
| 2004/0176766 A1 | 9/2004 | Shluzas |
| 2006/0293665 A1 | 12/2006 | Shluzas |
| 2010/0125302 A1 | 5/2010 | Hammill, Sr. et al. |

* cited by examiner

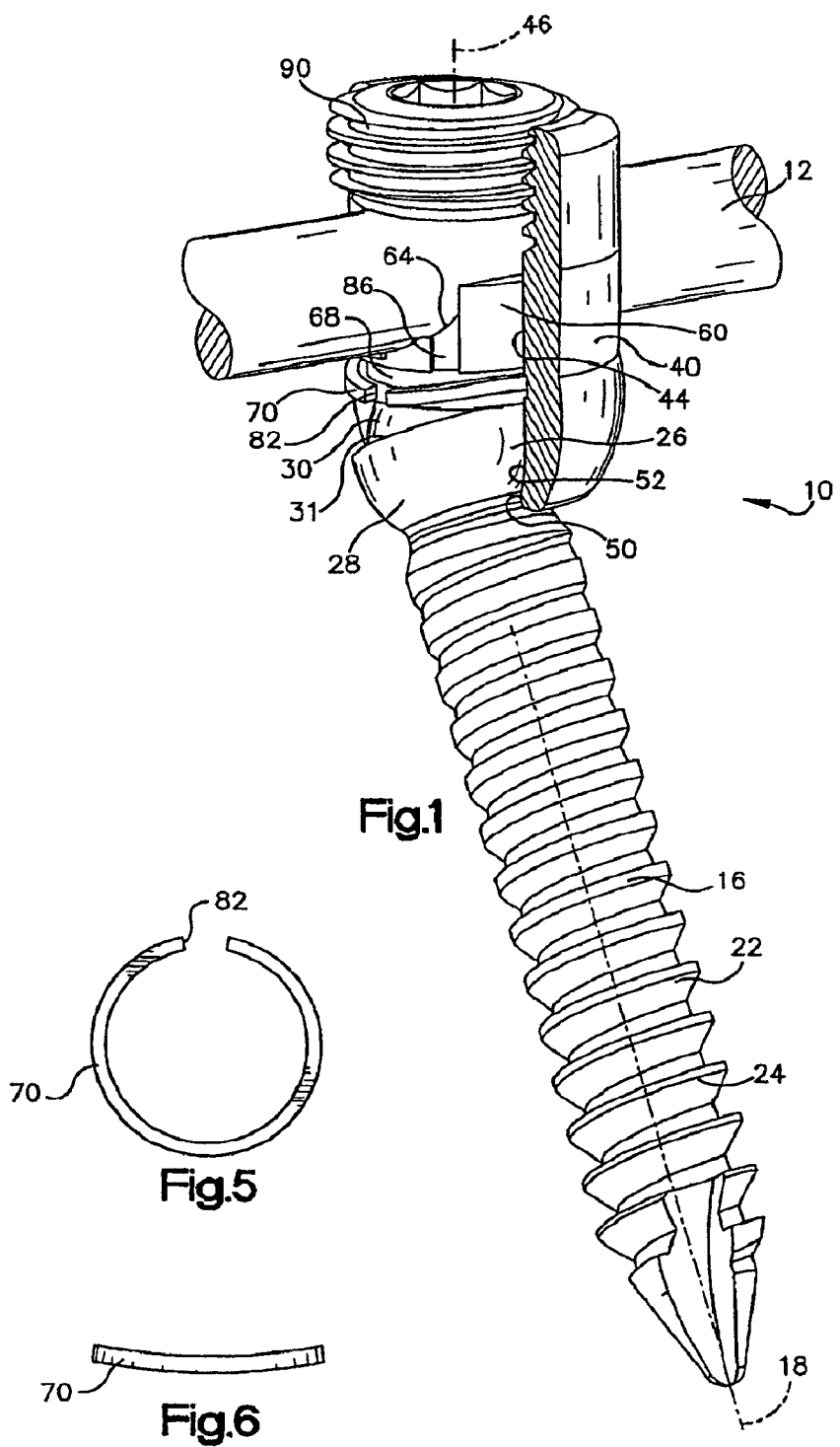

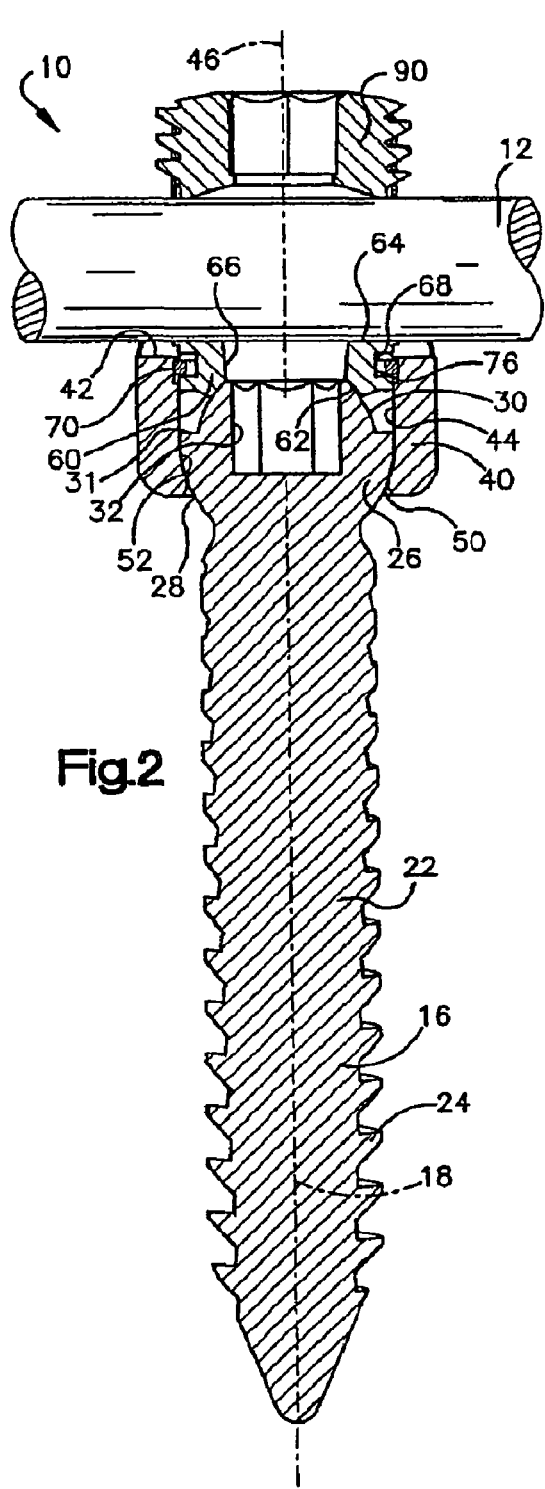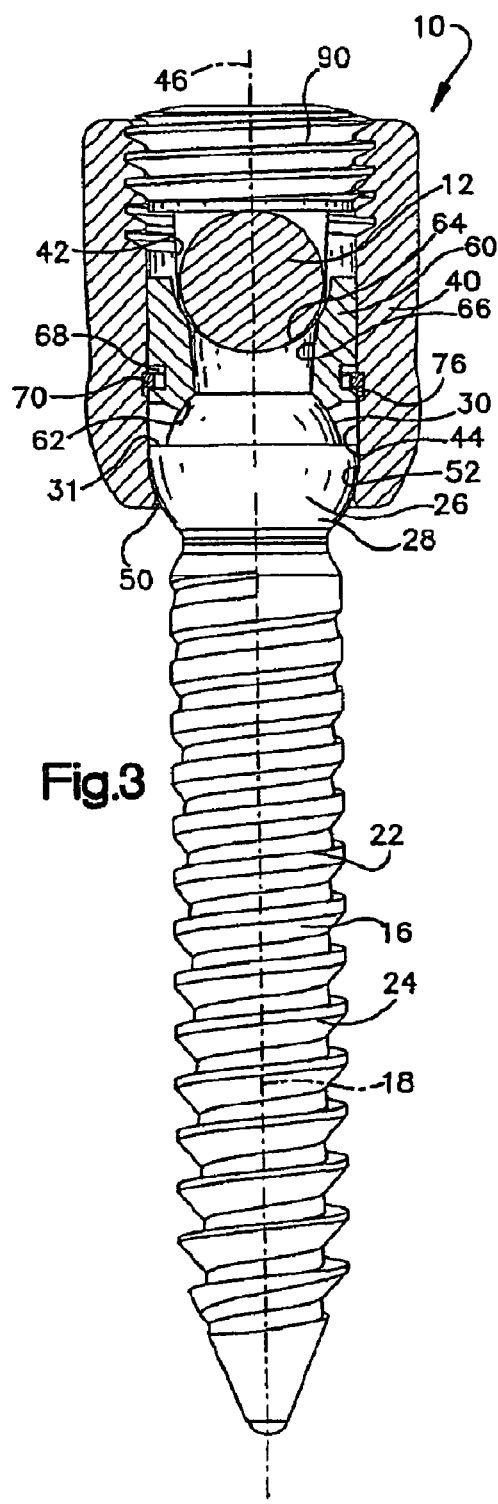

METHODS FOR CONNECTING A LONGITUDINAL MEMBER TO A BONE PORTION

CROSS-REFERENCE TO RELATED APPLICATION

This application is a continuation of U.S. application Ser. No. 11/415,676, filed May 2, 2006, now U.S. Pat. No. 7,879,075, which is a continuation of U.S. application Ser. No. 10/075,668, filed Feb. 13, 2002, now U.S. Pat. No. 7,066,937, which is incorporated by reference in its entirety.

TECHNICAL FIELD

The present invention relates to an apparatus which is used to retain bone portions, such as vertebrae of a spinal column, in a desired spatial relationship.

BACKGROUND OF THE INVENTION

A known apparatus for retaining vertebrae of a spinal column in a desired spatial relationship is disclosed in U.S. Pat. No. 6,280,442. U.S. Pat. No. 6,280,442 discloses an apparatus including a longitudinal member extendable along the spinal column. A fastener engageable with a vertebra of the spinal column connects the longitudinal member to the vertebra. A housing has a first passage through which the longitudinal member extends and a second passage with a longitudinal axis extending transverse to the first passage. The fastener extends through an opening in the housing into the second passage. The longitudinal axis of the fastener is positionable in any one of a plurality of angular positions relative to the longitudinal axis of the second passage.

A spacer received in the housing is engageable with the fastener and the longitudinal member. A clamping member threadably engages the housing to clamp the longitudinal member, the spacer, and the housing to the fastener to prevent movement of the fastener relative to the housing. When the longitudinal member is disengaged from the spacer, the housing may not remain in position relative to the fastener until the longitudinal member is clamped to the spacer. Accordingly, the housing must be held in position relative to the fastener by a surgeon while the longitudinal member is clamped to the spacer.

SUMMARY OF THE INVENTION

The present invention is an apparatus which is used to retain bone portions in a desired spatial relationship. The apparatus includes a longitudinal member connectable with a bone portion. A fastener having a longitudinal axis is engageable with the bone portion to connect the longitudinal member to the bone portion. A housing has a first passage configured to receive the longitudinal member. The housing has a second passage with a longitudinal axis extending transverse to the first passage. The fastener extends through an opening in the housing into the second passage and is movable relative to the housing. The longitudinal axis of the fastener is positionable in any one of a plurality of angular positions relative to the longitudinal axis of the second passage.

A spacer received in the second passage of the housing is engageable with the fastener and the longitudinal member. A member applies a force to prevent relative movement between the fastener and the housing when the longitudinal member is disengaged from the spacer and the spacer engages the fastener. The fastener and the housing are manually movable relative to each other against the force when the longitudinal member is disengaged from the spacer and the member applies the force. A clamping mechanism clamps the longitudinal member, the spacer, and the housing to the fastener to prevent movement of the fastener relative to the housing. Accordingly, the housing and the fastener can be positioned relative to each other and the member will hold the fastener and the housing in the relative positions before the longitudinal member is connected to the housing.

BRIEF DESCRIPTION OF THE DRAWINGS

The foregoing and other features of the present invention will become apparent to one skilled in the art to which the present invention relates upon consideration of the following description of the invention with reference to the accompanying drawings, wherein:

FIG. 1 is a perspective view of an apparatus constructed in accordance with the present invention with portions removed for clarity;

FIG. 2 is a sectional view of the apparatus of FIG. 1;

FIG. 3 is a part sectional view of the apparatus of FIG. 1;

FIG. 5 is a plan view of a spring member of the apparatus of FIG. 1; and

FIG. 6 is a side view of the spring member.

DESCRIPTION OF THE INVENTION

Figure 4:
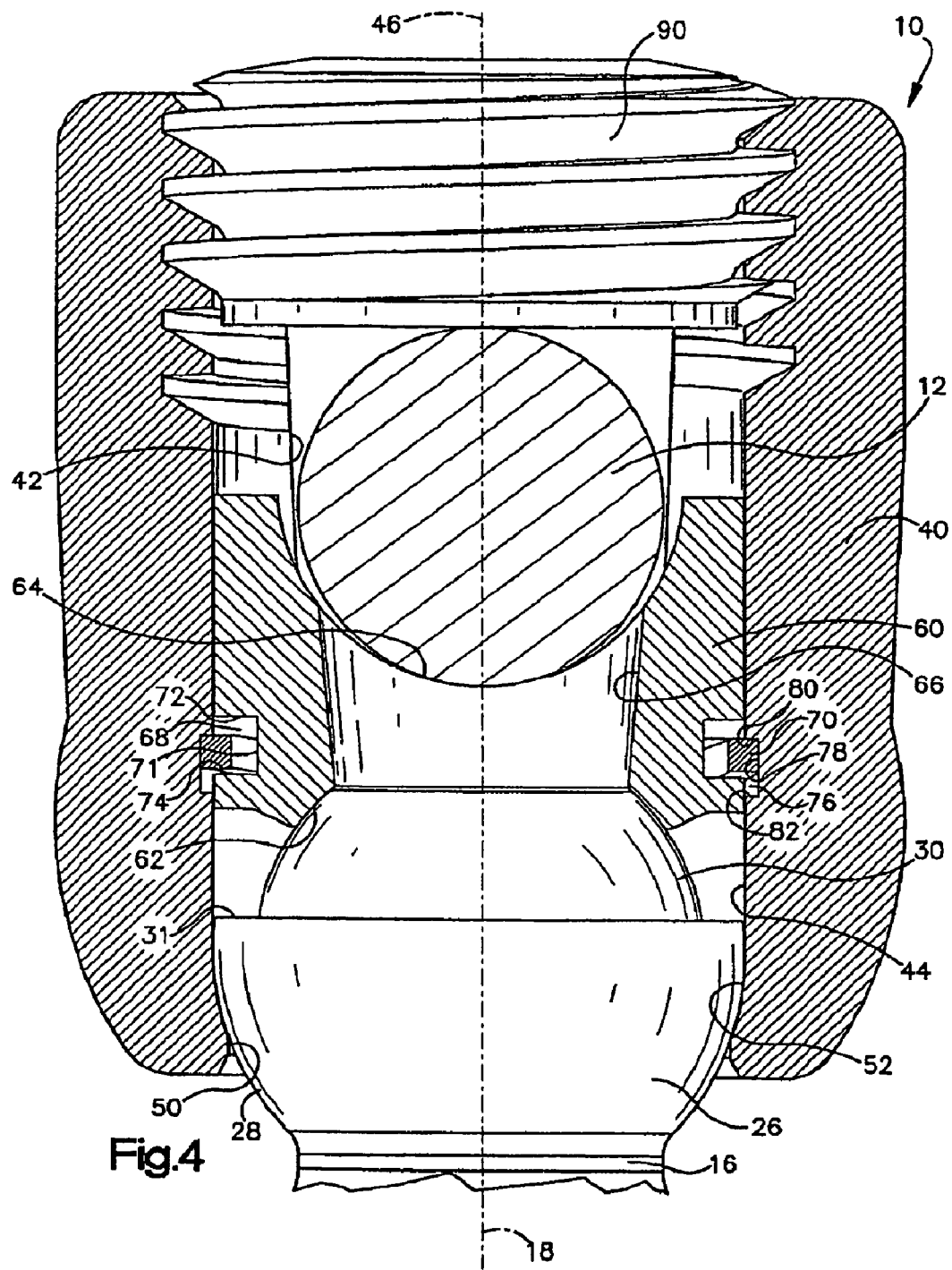
FIG. 4 is an enlarged sectional view of a portion of the apparatus of FIG. 1.

The present invention is directed to an apparatus for retaining bone portions, such as vertebrae of a spinal column, in a desired spatial relationship. FIGS. 1-4 illustrate an apparatus 10 constructed according to the present invention. The apparatus 10 includes a surgically implantable longitudinal member or rod 12 for maintaining bone portions, such as vertebrae of a spinal column, in a desired spatial relationship. The member 12 is connected with vertebrae of the spinal column by fasteners 16.

The rod 12 is made of a suitable biocompatible material and has a length which is at least sufficient to enable the rod to span at least two vertebrae. Of course, the length of the rod 12 in any particular installation will depend upon the condition to be corrected and the number of vertebrae to be held in a desired spatial relationship relative to each other by the rod.

The rod 12 (FIGS. 1-3) is connected to a respective vertebra by the fastener 16 made of a suitable biocompatible material. The fastener 16 has a longitudinal axis 18 and a threaded end portion 22 having a course thread convolution 24 which engages the vertebra. A second end portion 26 of the fastener 16 is provided with a first part spherical surface 28. The second end portion 26 of the fastener 16 also includes a second part spherical surface 30 having a diameter less than a diameter of the first part spherical surface 28. A radially extending shoulder 31 extends between the part spherical surfaces 28 and 30. A recess 32 (FIG. 2) is provided on the end portion 26 of the fastener 16. The recess 32 receives a tool (not shown) that applies torque to the fastener 16 to turn the thread convolution 24 into the vertebra.

The fastener 16 (FIGS. 1-4) extends into a housing 40 that interconnects the rod 12 and the fastener 16. The housing 40 (FIG. 2) has a first passage 42 through which the rod 12 extends. The housing 40 has a second passage 44 with a longitudinal axis 46 that extends transverse to the first passage 42. The fastener 16 extends through an opening 50 in the housing 40 and into the second passage 44. The first part spherical surface 28 of the fastener 16 engages a concave part spherical surface 52 of the housing 40. Accordingly, the fastener 16 is universally pivotable relative to the housing 40 so that the longitudinal axis 18 of the fastener 16 is positionable in any one of a plurality of angular positions relative to the longitudinal axis 46 of the passage 44.

A spacer 60 is housed in the second passage 44 of the housing 40. The spacer 60 (FIGS. 2-4) has a concave part spherical surface 62 that engages the part spherical surface 30 of the fastener 16. The shoulder 31 on the fastener 16 is engageable with the spacer 60 to limit the relative movement between the fastener and the housing 40. The spacer 60 also has a concave part cylindrical surface 64 that engages the rod 12. The spacer 60 has an opening 66 through which the tool (not shown) extends to engage the recess 32 in the fastener 16. The tool extends through the opening 66 to apply torque to the fastener 16 and connect the fastener to the vertebra.

The spacer 60 (FIG. 4) has a circumferential groove 68 for receiving a compressible member such as a spring member 70. The groove 68 is defined by an axially extending cylindrical surface 71. An upper surface 72 extends radially outward from the cylindrical surface 71. A lower surface 74 extends radially outward from the cylindrical surface 71 and generally parallel to the upper surface 72.

The housing 40 includes a circumferential groove 76 for receiving the spring member 70 so that the spring member extends from the groove 68 in the spacer 60 to the groove in the housing. The groove 76 is defined by an axially extending cylindrical surface 78. An upper surface 80 extends radially inward from the cylindrical surface 78. A lower surface 82 extends radially inward from the cylindrical surface 78 and generally parallel to the upper surface 80.

The spring member 70 (FIGS. 5 and 6) is a ring having a gap 82. The gap 82 permits the spring member 70 to radially contract and expand. The spring member 70 has an arched shape, as viewed in FIG. 6, when the spring member 70 is disengaged from the spacer 60 and the housing 40. When the spring member 70 is received in the grooves 68 and 76 (FIG. 4), the spring member engages the lower surface 74 on the spacer 60 and the upper surface 80 on the housing 40.

The spring member 70 applies an axial force to the spacer 60 to prevent relative movement between the fastener 16 and the housing 40 when the rod 12 is disengaged from the spacer and the spacer engages the fastener. The spring member 70 urges the spacer 60 axially toward the fastener 16 and the part spherical surface 52 of the housing 40 against the part spherical surface 28 of the fastener. The part spherical surface 62 of the spacer 60 frictionally engages the part spherical surface 30 of the fastener 16 and the part spherical surface 28 of the fastener frictionally engages the part spherical surface 52 of the housing 40. The fastener 16 and the housing 40 are manually movable relative to each other by a surgeon when the rod 12 is disengaged from the spacer 60 and the spring member 70 applies the axial force. The force applied by the spring member 70 may be overcome by the surgeon to move the housing 40 relative to the fastener 16. Accordingly, the housing 40 can be positioned relative to the fastener 16 and held in position relative to the fastener by the spring member 70 without the rod 12 engaging the spacer 60. It is contemplated that any compressible member could be used to apply the force to the fastener 16 to prevent relative movement between the fastener and the housing 40 when the rod 12 is disengaged from the spacer 60.

The spacer 60 has four axially extending slots 86, one of which is shown in FIG. 1. The slots 86 intersect the groove 68. A tool (not shown) has four prongs that extend through the slots 86 and into engagement with the spring member 70. The tool grasps the spacer 60 and the spring member 70 for inserting the spacer and the spring member into the housing 40. The prongs of the tool engage the spring member 70 to radially contract the spring member into the groove 68 in the spacer 60. The prongs hold the spring member 70 in the radially contracted condition in the groove 68 while the spacer 60 and spring member are being inserted into the housing 40. Once the spacer 60 engages the fastener 16, the prongs are removed from the slots 86 and the spring member 70 radially expands into the groove 71 in the housing 40. Although the spacer 60 is described as having four slots 86, the spacer could have any number of slots and the tool would have the same number of prongs as the spacer has slots.

A clamping mechanism or set screw 90 (FIGS. 1-4) threadably engages the housing 40. The set screw 90 and the housing 40 have a German standard DIN513 buttress thread. It is contemplated that the set screw 90 and the housing 40 could have any desired thread formation. The set screw 90 engages and applies a force to the rod 12 to press the rod against the spacer 60 and the spacer against the fastener 16. The set screw 90 clamps the rod 12, the spacer 60, and the housing 40 to the fastener 16 to prevent movement of the fastener relative to the housing. The force applied by the set screw 90 cannot be overcome by the surgeon to move the housing 40 relative to the fastener 16.

The apparatus 10 is assembled by inserting the fastener 16 through the opening 50 in the housing 40 so that the part spherical surface 28 of the fastener engages the part spherical surface 52 of the housing. The spacer 60 and the spring member 70 are inserted into the housing 40 by radially compressing the spring member into the groove 68 in the spacer. The spacer 60 and the spring member 70 are inserted into the second passage 44 until the part spherical surface 62 of the spacer engages the part spherical surface 30 of the fastener 16. The spring member 70 is released and expands radially into the groove 76 in the housing 40.

A tool is inserted through the opening 66 in the spacer 60 and into the recess 32 in the fastener 16. Torque is applied to the fastener 16 to turn the thread convolution 24 into the vertebra. Once the fastener 16 is connected with the vertebra, the housing 40 can be positioned relative to the fastener. The spring member 70 maintains the position of the housing 40 relative to the fastener 16 while the rod 12 is disengaged from the spacer 60. Once the housing 40 is positioned relative to the fastener 16, the rod 12 is placed into the passage 42 and in engagement with the spacer 60. The set screw 90 is threaded into the housing 40 and into engagement with the rod 12. The set screw 90 clamps the rod 12, the spacer 60, and the housing 40 to the fastener 16 to prevent movement of the fastener relative to the housing. Alternatively, the fastener 16 may be connected to the vertebra prior to the spacer 60 and the spring member 70 being inserted into the housing 40.

From the above description of the invention, those skilled in the art will perceive improvements, changes and modifications. Such improvements, changes and modifications within the skill of the art are intended to be covered by the appended claims.

What is claimed is:

1. An apparatus for connecting a longitudinal member with a bone portion, comprising:
   a fastener having a longitudinal axis and engageable with the bone portion to connect said longitudinal member to the bone portion;
   a housing having a first passage configured to receive said longitudinal member and a second passage with a longitudinal axis transverse to said first passage, said fastener extending through an opening in said housing into said second passage, the housing having a first engaging surface extending transverse to the longitudinal axis of the second passage, the first engaging surface positioned such that when the fastener is seated in the housing, the first engaging surface is proximal of a proximal end of the fastener;

a spacer received in said second passage of said housing and engageable with said fastener and said longitudinal member, said spacer having a second engaging surface extending transverse to the longitudinal axis of the second passage; and a biasing element contacting the first engaging surface of the housing thereby limiting proximal movement of the spacer and fastener, the biasing element contacting the second engaging surface of the spacer thereby limiting distal movement of the spacer and fastener, the biasing element applying a force biasing the spacer towards the fastener, thereby holding said longitudinal axis of said fastener in any one of a plurality of desired angular positions relative to said longitudinal axis of said second passage when said longitudinal member is disengaged from said spacer and said spacer engages said fastener, said fastener and said housing being manually movable relative to each other against said force when said longitudinal member is disengaged from said spacer and said biasing element applies said force.

2. The apparatus of claim 1, wherein said biasing element is an axially compressible member.

3. The apparatus of claim 1, wherein said biasing element is a spring member.

4. The apparatus of claim 1, wherein the housing includes a substantially U-shaped opening sized to accept said longitudinal member, wherein said spacer includes a concave upper surface configured to receive said longitudinal member, said concave upper surface extending into said U-shaped opening.

5. The apparatus of claim 1, wherein said housing includes an internal thread, and said apparatus further includes a threaded compression element engageable with said internal thread.

6. An apparatus for connecting a longitudinal member with a bone portion, comprising:

a fastener having a longitudinal axis and engageable with the bone portion to connect said longitudinal member to the bone portion;

a housing having a first passage configured to receive said longitudinal member and a second passage configured to receive said fastener, said fastener extending through an opening in said housing into said second passage, the housing having a pocket in an inner wall, the pocket having an upper surface, the pocket positioned such that when the fastener is seated in the housing, at least the upper surface of the pocket is proximal of a proximal end of the fastener;

a spacer received in said second passage of said housing and engageable with said fastener and said longitudinal member, said spacer having a pocket with a height extending in a direction along the second passage of the housing; and a biasing element contacting the upper surface of the housing pocket and the pocket of the spacer, the biasing element having a height extending in the direction of the second passage, the biasing element height being less than the height of the spacer pocket such that the biasing element may move proximally and distally within the spacer pocket, the biasing element applying a force biasing the spacer towards the fastener, thereby holding said longitudinal axis of said fastener in any one of a plurality of desired angular positions relative to a longitudinal axis of said second passage when said longitudinal member is disengaged from said spacer and said spacer engages said fastener, said fastener and said housing being manually movable relative to each other against said force when said longitudinal member is disengaged from said spacer and said biasing element applies said force.

7. The apparatus of claim 6, wherein said biasing element is an axially compressible member.

8. The apparatus of claim 6, wherein said biasing element is a spring member.

9. The apparatus of claim 6, wherein the housing includes a substantially U-shaped opening sized to accept said longitudinal member, wherein said spacer includes a concave upper surface configured to receive said longitudinal member, said concave upper surface extending into said U-shaped opening.

10. The apparatus of claim 6, wherein said housing includes an internal thread, and said apparatus further includes a threaded compression element engageable with said internal thread.

11. The apparatus of claim 6, wherein the biasing element contacting the upper surface of the housing pocket limits proximal movement of the spacer and fastener, and the biasing element contacting a lower surface of the spacer pocket limits distal movement of the spacer and fastener.

12. An apparatus for connecting a longitudinal member with a bone portion, comprising:

a fastener having a longitudinal axis and engageable with the bone portion to connect said longitudinal member to the bone portion;

a housing having a first passage configured to receive said longitudinal member and a second passage configured to receive said fastener, said fastener extending through an opening in said housing into said second passage, the housing having a pocket in an inner wall, the pocket having proximal and distal surfaces and a height measured therebetween, the pocket positioned such that when the fastener is seated in the housing, at least the proximal surface of the pocket is proximal of a proximal end of the fastener;

a spacer received in said second passage of said housing and engageable with said fastener and said longitudinal member, said spacer having a pocket in an outer wall, the pocket having proximal and distal surfaces and a height measured therebetween; and a biasing element received in the housing and spacer pockets, the biasing element having a height measured in the same direction as the heights of the housing and spacer pockets, wherein the biasing element height is less than the height of the housing pocket and the spacer pocket respectively, wherein the biasing element applies a force biasing the spacer towards the fastener, thereby holding said longitudinal axis of said fastener in any one of a plurality of desired angular positions relative to a longitudinal axis of said second passage when said longitudinal member is disengaged from said spacer and said spacer engages said fastener, said fastener and said housing being manually movable relative to each other against said force when said longitudinal member is disengaged from said spacer and said biasing element applies said force and wherein the biasing element contacts the proximal surface of the housing pocket to prevent proximal movement of the spacer and fastener, and the biasing element contacts the distal surface of the spacer pocket to limit distal movement of the spacer and fastener.

13. The apparatus of claim 12, wherein said biasing element is an axially compressible member.

14. The apparatus of claim 12, wherein said biasing element is a spring member.

15. The apparatus of claim 12, wherein the housing includes a substantially U-shaped opening sized to accept said longitudinal member, wherein said spacer includes a concave upper surface configured to receive said longitudinal member, said concave upper surface extending into said U-shaped opening.

16. The apparatus of claim 12, wherein said housing includes an internal thread, and said apparatus further includes a threaded compression element engageable with said internal thread.

\* \* \* \* \*